(12) United States Patent
Copar et al.

(10) Patent No.: US 8,410,285 B2
(45) Date of Patent: *Apr. 2, 2013

(54) 2'-HALOBIPHENYL-4-YL INTERMEDIATES IN THE SYNTHESIS OF ANGIOTENSIN II ANTAGONISTS

(75) Inventors: Anton Copar, Ljubljana (SI); Zdenko Casar, Ljubljana (SI); Andrej Premrl, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 13 days.

This patent is subject to a terminal disclaimer.

(21) Appl. No.: 12/933,617

(22) PCT Filed: Mar. 19, 2009

(86) PCT No.: PCT/EP2009/053267

§ 371 (c)(1),
(2), (4) Date: Dec. 8, 2010

(87) PCT Pub. No.: WO2009/115584

PCT Pub. Date: Sep. 24, 2009

(65) Prior Publication Data

US 2011/0105539 A1      May 5, 2011

(30) Foreign Application Priority Data

Mar. 20, 2008 (EP) .................... 08153084
Mar. 20, 2008 (EP) .................... 08153085

(51) Int. Cl.
  *C07D 235/08*  (2006.01)
(52) U.S. Cl. ................................... 548/305.4
(58) Field of Classification Search ........ 548/305.4
See application file for complete search history.

(56) References Cited

FOREIGN PATENT DOCUMENTS

| | | |
|---|---|---|
| EP | 0502314 A1 | 9/1992 |
| EP | 1719766 A2 | 11/2006 |
| WO | WO 2004/087676 A | 10/2004 |
| WO | WO 2006/044648 A1 | 4/2006 |
| WO | WO 2006/103068 A | 10/2006 |

OTHER PUBLICATIONS

CA 36:12402 (1942).*
E.J. Corey; Robert Robinson Lecture Retrosynthetic Thinking—Essentials and Examples; Chem. Soc. Rev., 1988, vol. 17, pp. 111-133.
Marino A. Campo et al.; Synthesis of Fluoren-9-ones via Palladium-Catalyzed Cyclocarbonylation of o-Halobiaryls; Organic Letters 2000; vol. 2, No. 23; pp. 3675-3677.
Jwanro Hassan et al; Aryl-Aryl Bond Formation One Century After the Discovery of the Ullmann Reaction; Chem. Rev., 2002, vol. 102, pp. 1359-1469.
European Search Report: International Application No. PCT/EP2009/053269, Jun. 4, 2009.

* cited by examiner

*Primary Examiner* — Laura L. Stockton
(74) *Attorney, Agent, or Firm* — Arent Fox LLP

(57) ABSTRACT

A process for obtaining 2'-halo-4-methylbiphenyls is described, which comprises reacting 4 halotoluene with a 1,2-dihalobenzene in the presence of elemental metal such as magnesium, lithium or zinc, wherein 0 to 0.9 molar, particularly 0 to 0.2 molar excess of 4-halotoluene in regard to 1,2-dihalobenzene is used, and arised organometal intermediates are quenched by elemental mental halogen. In addition, the coupling of arised 2'-halo-4-methylbiphenyls with 2-(1-propyl)-4-methyl-6-(1'-methylbenzimidazole-2-il)benzimidazole to afford 3'-(2'-halo-biphenyl-4-ylmethyl)-1,7'-dimethyl-2'-propyl-1H,3'H-[2,5']bibenzoimidazolyl, which can be further converted to organometallic compound and said organometallic compound is further reacted with formic acid derivative, such as N,N-dimethylformamide, alkylformiate or carbon dioxide to obtain telmisartan, is also described. Further described is use of in line analytics for monitoring the aforementioned reactions, process for preparing a pharmaceutical composition and/or dosage for, or use in preparing a medicament.

4 Claims, No Drawings

2'-HALOBIPHENYL-4-YL INTERMEDIATES IN THE SYNTHESIS OF ANGIOTENSIN II ANTAGONISTS

CROSS-REFERENCE TO RELATED APPLICATION

This is a National Stage entry of International Application No. PCT/EP2009/053267, filed Mar. 19, 2009, the contents of the prior application are hereby incorporated herein in their entirety by reference.

FIELD OF THE INVENTION

The present invention relates in general to the field of organic chemistry and in particular to the preparation of substituted biphenyls, in particular to 4-halomethyl-2'-halobiphenyl and their use as intermediates in preparation of angiotensin II antagonists. The invention also relates to halo and organometal intermediates for preparing telmisartan. Further the invention relates to use of in line analytics. In addition, the invention relates to the process for preparing pharmaceutical composition and/or dosage form comprising the process for preparing said biphenyls or intermediates. The embodiments of the present invention can be beneficially applied also for preparing a medicament.

BACKGROUND OF THE INVENTION

Angiotensin II antagonists ("sartans") are efficient active compounds with biological activity which has proved useful for the treatment of hypertension. Most of commercially available sartans contain biphenyl moiety substituted with 5-tetrazolyl or carboxy group on the position 2' (Formula 1, X is COOH or 5-tetrazolyl).

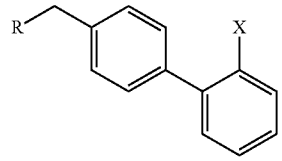

Formula 1

R = sartan specific core

Telmisartan or salt or ester thereof (TLM, Formula 2) known from EP 502314 and which can be prepared in accordance with this invention is used as a pharmaceutical compound alone or in combination with pharmaceutically acceptable carrier for treatment of hypertension in human or animal and functions as angiotensin II antagonists.

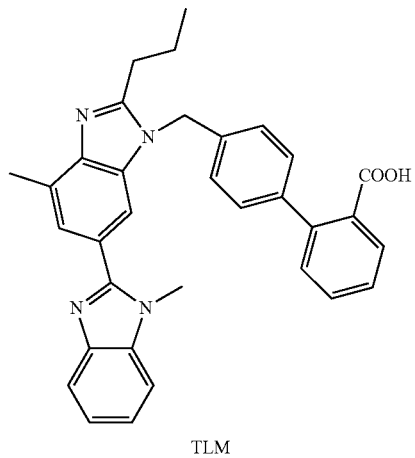

Formula 2

TLM

2'-halo-4-methylbiphenyls (Formula 3, X=Cl, Br, I) are potential starting materials for the synthesis of biphenyl type sartans but they have not found an application in industry due to inefficient or expensive synthesis. Known procedures use Suzuki and Heck couplings which need for industry unfriendly boron and tin compounds, Ullmann reaction (Chem. Rev. 2002, 102, 1359-1469) give low yields and coupling of Grignard intermediates require significant amounts of starting materials (Org. Lett. 2000, 2, 3675-3677). The later reaction was exercised using 1,2-dihalobenzene, 4-halotoluene in the presence of magnesium and iodine for quenching the Grignard intermediate wherein 1,2-dihalobenzene, 4-halotoluene and iodine were used in the ratio of 1:2:3, which is not economically favorable for industrial application.

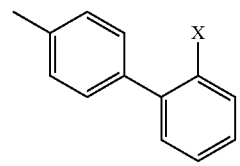

Formula 3

There is a need for efficient synthesis of biphenyl class of sartans especially for carboxy group containing derivatives such as telmisartan.

DISCLOSURE OF THE INVENTION

An aspect of the invention is a process for obtaining 2'-halo-4-methylbiphenyls, in which a 4-halotoluene is reacted with a 1,2-dihalobenzene in the presence of magnesium, lithium, zinc, cobalt or copper and optionally a catalyst, wherein less than 1 molar excess of 4-halotoluene in regard to 1,2-dihalobenzene is used, and arisen organometal intermediates are quenched by elemental halogen. Preferably less than 0.9 molar excess, particularly less than 0.2 molar excess of 4-halotoluene in regard to 1,2-dihalobenzene is used. Proportionally for each 1 mol of 1,2-dihalobenzene used in the reaction less than 2.9 mol; particularly from 1 to 2 mol, preferably 1 mol of elemental halogen is used to quench the organometal intermediate. The reaction is carried out in ether solvent or in a mixture of aprotic solvents comprising ether. Halo is selected from iodo, bromo or chloro.

Another aspect of the invention is a process for the synthesis of telmisartan, losartan, irbesartan, candesartan, olmesartan, valsartan or tasosartan or salt, ester or amide thereof, comprising preparing 4'-halomethyl-2-halo-biphenyl according to above aspect and converting it to said compound.

In another aspect the invention is a process for obtaining 3'-(2'-halo-biphenyl-4-ylmethyl)-1,7'-dimethyl-2'-propyl-1H,3'H-[2,5']bibenzoimidazolyl (TLMH) comprising coupling 2-(1-propyl)-4-methyl-6-(1'-methylbenzimidazole-2-yl)benzimidazole and 4'-halomethyl-2-halo-biphenyl.

In a further aspect the invention is a process for obtaining telmisartan characterized in that 3'-(2'-halo-biphenyl-4-ylmethyl)-1,7'-dimethyl-2'-propyl-1H,3'H-[2,5']bibenzoimidazolyl is converted to organometallic compound (TLMM) and said organometallic compound is further reacted with formic acid ester or amide, such as N,N-dimethylformamide, alkyl formate, and oxidized, or with carbon dioxide. Specifically said conversion is done with magnesium to Grignard reagent, or with Grignard reagent by halogen/metal-exchange reaction to another Grignard reagent, or with zinc to organozinc reagent; or preferably said conversion is done with lithium to organolithium reagent, or with organolithium reagent by halogen/metal-exchange reaction to another organolithium reagent; Halo is selected from iodo, bromo or chloro, specifically iodo.

Another aspect of the invention is use of formula TLMM for the synthesis of telmisartan or salt, ester or amide thereof.

In yet another aspect the invention is a compound of formula 4.

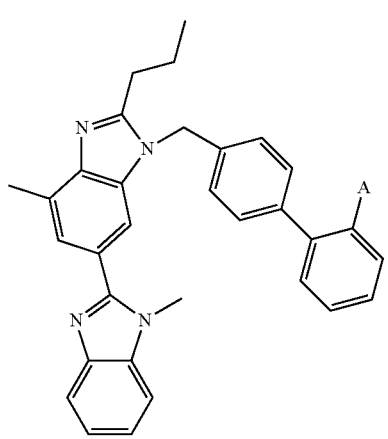

Formula 4

A = X, Li, MgX, ZnX; X = Cl, Br, I.

Another aspect of the invention is use of compound 4'-halomethyl-2-halo-biphenyl for the preparation of other sartans, such as losartan, irbesartan, candesartan, olmesartan, valsartan, tasosartan, salt, ester or other derivative thereof, or other compounds, that can be derived from the 4'-halomethyl-2-halo-biphenyl, wherein halo is selected from iodo, bromo or chloro and 4'-halomethyl-2-halo-biphenyl is not 4'-bromomethyl-2-iodo-biphenyl or 4'-bromomethyl-2-chloro-biphenyl.

Further aspect of the invention is in line analytic used to monitor the mentioned reactions and single components (reactants, intermediates, product and impurities) and/or for adjustment of reaction times or reaction temperatures in the said reactions.

Additional aspect of the present invention is a process for obtaining a pharmaceutical composition and/or dosage form comprising preparing telmisartan or salt thereof according above aspects; or obtaining 2'-halo-4-methylbiphenyls according to above aspects, and converting it to telmisartan; or preparing telmisartan, losartan, irbesartan, candesartan, olmesartan, valsartan, tasosartan or salt, ester or amide thereof according to above aspects, and mixing it, optionally in combination with another active pharmaceutical ingredient, with pharmaceutical excipient.

The present invention provides also the aspect of use of any of the aforementioned aspects for preparing a medicament.

DETAILED DESCRIPTION OF THE INVENTION

Surprisingly it has been found that 2'-halo-4-methylbiphenyls can be obtained in a simple one-pot two-step technical process, in yields that are industrially applicable and competitive in which a 4-halotoluene is reacted with a 1,2-dihalobenzene in the presence of magnesium, lithium, zinc, cobalt or copper, and optionally a catalyst selected from a transition metal compound, preferably a manganese, cobalt or copper compound, wherein less than 1, particularly less than 0.9 molar, particularly less than 0.2 molar excess of 4-halotoluene with regard to 1,2-dihalobenzene is used, that for each mol of 1,2-dihalobenzene, from 1.0 to 1.9, particularly from 1.0 to 1.2 mol 4-halotoluene is used, more particularly from 1.05 to 1.15 mol, and arisen organometal intermediates are quenched proportionally for each 1 mol of 1,2-dihalobenzene by less than 2.9 mol, particularly 1-2 mol, about 1 mol of elemental halogen.

The catalyst optionally used can be a palladium, copper, manganese, ruthenium, chromium, nickel compound, or the like.

Suprisingly it was noted that when the molar excess of 4-halotoluene with regard to 1,2-dihalobenzene is less than 1, preferably less than 0.9, more preferably less than 0.2, it significantly improves the reaction yield. The reason might be that the organometal reaction is a complex reaction and its yield depends on the ratio of reactants. In the case of the prior art ratio, when it was for 1,2-dihalobenzene to 4-halotoluene 1:2, the high excess of starting reactants like 4-halotoluene could induce transmetalation. Metalated 1,2-dihalobenzene could produce symmetric dimeric products in one side while liberated 4-halotoluene could consume more metal or produce symmetric dimeric products with prepared 4-metalated toluene on the other side. Such side reaction may considerably reduce yield and quality. Thus, reducing the molar excess of the 4-halotoluene in the metalo reaction surprisingly improved utility of the reaction in the industry. Further, it was unexpectedly observed that less halogen is needed to sufficiently quench the reaction, when the ratio of the starting reagents is changed.

The present invention provides a process for obtaining 2'-halo-4-methylbiphenyl in which 1 to less than 2 eq. of 4-halotoluene is dissolved in an aprotic solvent, which may be selected from tetrahydrofuran, methyltetrahydrofuran, diethylether, diisopropylether, methyl tertiary butyl ether, dibutyl ether or diphenyl ether and the solution is maintained at about 15° C. to 80° C., preferably at room temperature. 4-halotoluene can be selected from p-bromotoluene, p-chlorotoluene or p-iodotoluene. 2 to 5 eq of metal is added and stirred for about 5 to 180 minutes. By the term metal there is contemplated any embodiment capable of forming organometal intermediates such as, e. g. magnesium, lithium or zinc. To thus prepared mixture one adds 1 eq. of 1,2-dihalobenzene dissolved in up to in the said solvent dropwise at 15° C. to 80°

C., preferably at 50 to 60° C. during 1 min to 5 hours, such as during 2 hours and stirred at same temperature for 1 to 48 hours. Dihalobenzene can be selected from 1-bromo-2-chlorobenzene, 1-chloro-2-iodobenzene, 1-bromo-2-iodobenzene, 1,2-dibromobenzene, or 1,2-diiodobenzene. To the solution of thus obtained 4'-methyl-biphenyl-2-ylmetal halide in the said solvent 1 to 5 eq of elemental halogen is added at 15° C. to 80° C., preferably at room temperature. 4'-methyl-biphenyl-2-ylmetal halide can be any appropriate organometal compound such as, e. g. 4'-methyl-biphenyl-2-ylmagnesium halide, wherein halide may be iodide, bromide or chloride, preferably bromide. Elemental halogen is selected from iodine ($I_2$) or bromine ($Br_2$) or chlorine ($Cl_2$). The mixture is stirred for minimum 5 minutes. The remaining halogen is reduced with aqueous solution of $NaHSO_3$ or $Na_2S_2O_3$. After work-up with water and an apolar solvent which may be selected from esters, ethers, chlorinated solvents and hydrocarbons preferably from aliphatic hydrocarbons such as n-hexane, n-pentane, n-heptane, cyclohexane, methylcyclohexane are added. The phases are separated and the organic phase is evaporated. The product is for example purified with LPLC chromatography. Mobile phase is n-hexane, stationary phase is silica gel 60. The fractions are followed by TLC method and collected. The main fractions are evaporated to give 2-halo-4'methyl-biphenyl in yield off at least 60%.

In a more specific but preferred example 1.1 eq of 4-bromotoluene is dissolved in 5 to 7 times bigger volume of tetrahydrofuran and the solution is maintained at room temperature. 2.5 eq of Mg is added and stirred for at least 30 minutes. To thus prepared mixture one adds 1 eq of 1-bromo-2-chlorobenzene diluted by the same volume of tetrahydrofurane dropwise at 55° C. during 2 hours and stirred at same temperature for 1 to 3 hours. To the solution of thus obtained 4'-methyl-biphenyl-2-ylmagnesium bromide in tetrahydrofuran 1 eq of iodine ($I_2$) is added and the reaction is worked up as described above.

The employment of excess of only 0.1 eq of 4-halotoluene dramatically improves the yield, which exceeds in this specific example 60%. Furthermore, only 1 eq of halogen was sufficient to quench the reaction, which lasts 3 hours at most. The procedure is a great improvement of known literature procedures (Org. Lett. 2000, 2, 3675-3677) which takes 14 hours to react and uses over two times excess of 4-halotoluene and three times excess of halogen to achieve comparable yields.

In additional reactions obtained 2-halo-4'methyl-biphenyl is halogenated in dichloromethane yielding 4'-halomethyl-2-halo-biphenyl. Specific compounds thus prepared are 4'-bromomethyl-2-bromo-biphenyl, 4'-iodomethyl-2-iodo-biphenyl, 4'-iodomethyl-2-bromo-biphenyl, 4'-iodomethyl-2-chloro-biphenyl, 4'-chloromethyl-2-iodo-biphenyl, 4'-chloromethyl-2-bromo-biphenyl, 4'-chloromethyl-2-chloro-biphenyl. In one embodiment, said 4'-halomethyl-2-halo-biphenyl can be reacted with 2-(1-propyl)-4-methyl-6-(1'-methylbenzimidazole-2-il)benzimidazole (PMB), to afford TLMH.

In a specific embodiment the invention also provides for coupling of 2-halo-4'-bromomethyl-biphenyl and 2-(1-propyl)-4-methyl-6-(1'-methylbenzimidazole-2-il)benzimidazole, which is performed but not limited as follows: 10-25 mL of sulfolane (tetramethylene sulfone) or N,N-dimethylacetamide or N-methyl-2-pyrrolidone or dimethyl sulfoxide is charged to the flask. 0.85 g of 2-(1-propyl)-4-methyl-6-(1'-methylbenzimidazole-2-il)benzimidazole and 0.38 g of strong base such as KtBuO or appropriate amount of NaOH, KOH, LiOH, $Na_2CO_3$, $K_2CO_3$, $NaHCO_3$ or $KHCO_3$ are added. The mixture is brought to the temperature of about 25° C.-45° C. to dissolve all the components. The solution is then brought to the temperature of about 5° C. to 25° C. and from 1 to 1.2 equivalents of 2-halo-4'-bromomethyl-biphenyl in 5 to 20 mL of solvent is added during 0.5-5 hours. The reaction mixture is stirred at the same temperature for additional 0-5 hours. 40 mL of demineralised water and 35 mL of ethyl acetate are added. The phases are separated. The EtOAc phase is washed several times with saturated water solution of NaCl. The solvent is evaporated and 4 mL mixture of EtOAc and acetone is added. The suspension is stirred for 15 minutes to 5 hours. The precipitate is filtered off and dried to give TLMH.

In a preferred example telmisartan is prepared from the intermediate 3'-(2'-halo-biphenyl-4-ylmethyl)-1,7'-dimethyl-2'-propyl-1H,3'H-[2,5']bibenzoimidazolyl (TLMH) by introducing C-1 synthon in high oxidation state in one-pot two-step procedure on the position 2'. Scheme 1 represents the synthesis of TLMH.

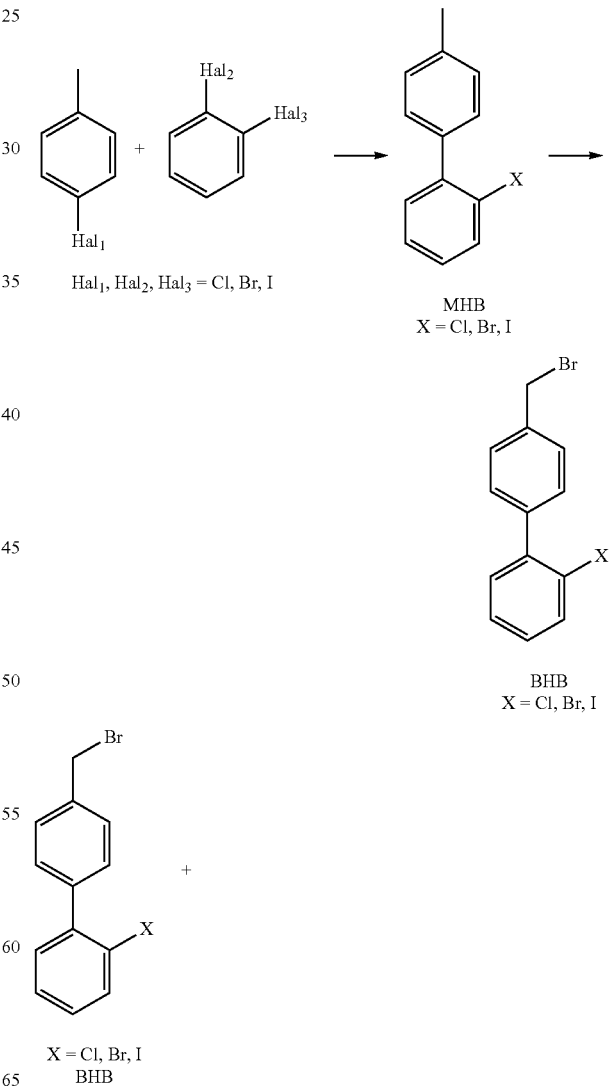

Scheme 1

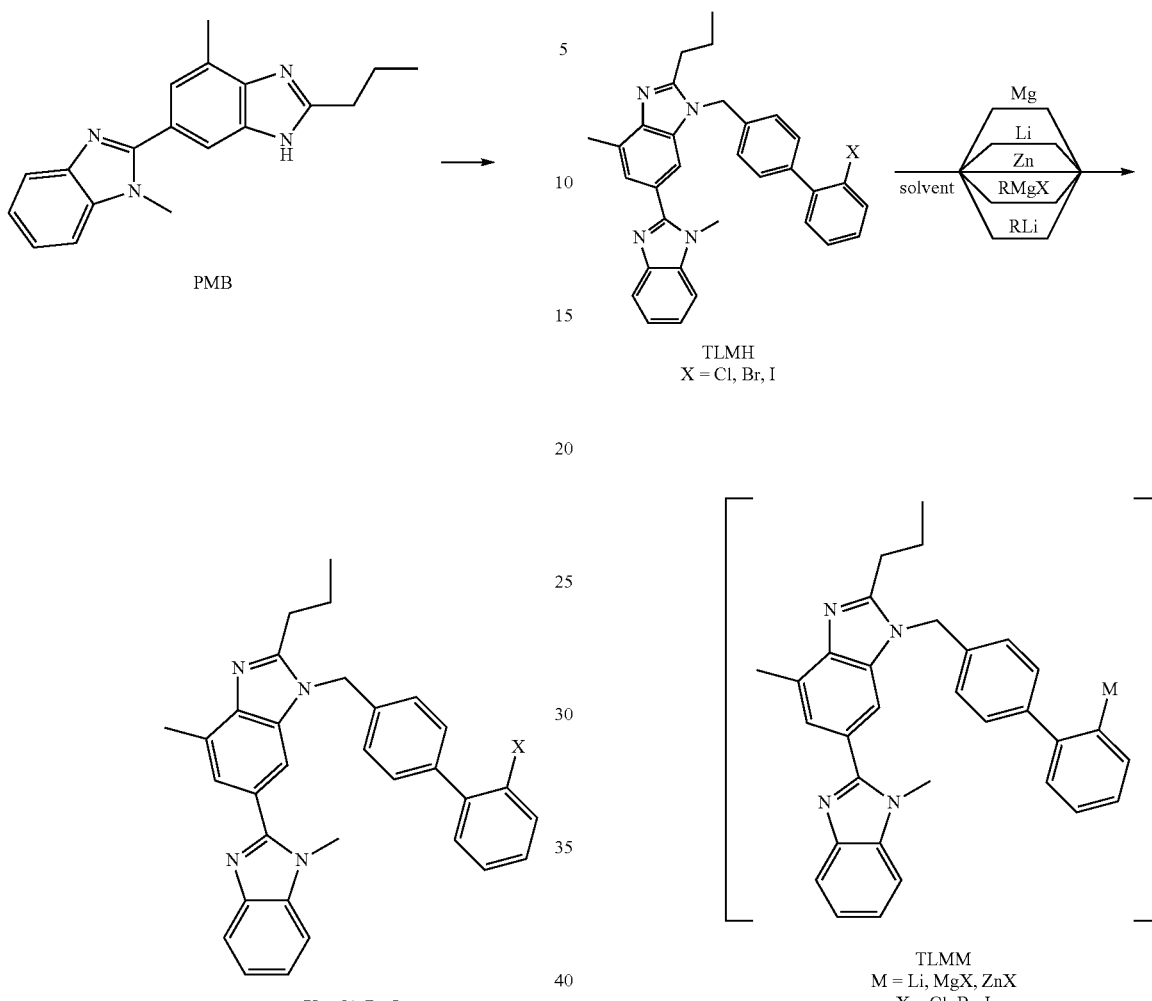

TLMH is further converted to organometallic compound TLMM as presented in Scheme 2 which is further reacted with formic acid derivative such as ester or amide, preferably N,N-dimethylformamide, or carbon dioxide in the second step as presented in Scheme 3.

Formula 4 encompasses embodiments TLMH and TLMM, wherein TLMH is halo substituted on the 2' position of 3'-(biphenyl-4-ylmethyl)-1,7'-dimethyl-2'-propyl-1H,3'H-[2,5']bibenzoimidazolyl, representing 3'-(2'-halo-biphenyl-4-ylmethyl)-1,7'-dimethyl-2'-1H,3'H-[2,5']bibenzoimidazolyl, and TLMM is Li, MgX or ZnX substituted on the 2' position of the biphenyl part of 3'-(biphenyl-4-ylmethyl)-1,7'-dimethyl-2'-propyl-1H,3'H-[2,5']bibenzoimidazolyl, wherein X is selected from iodo, bromo or chloro. Metals for creating organometallic intermediate are selected from alkali, earth-alkali, transition metals or lantanides. In created organometallic compounds of type TLM-Met, TLM-MetX or (TLM)$_2$-Met TLM means decarboxytelmisartan radical, Met is metal (monovalent or bivalent respectively) and X is chloro, bromo or iodo. Preferred metals are lithium, magnesium or zinc.

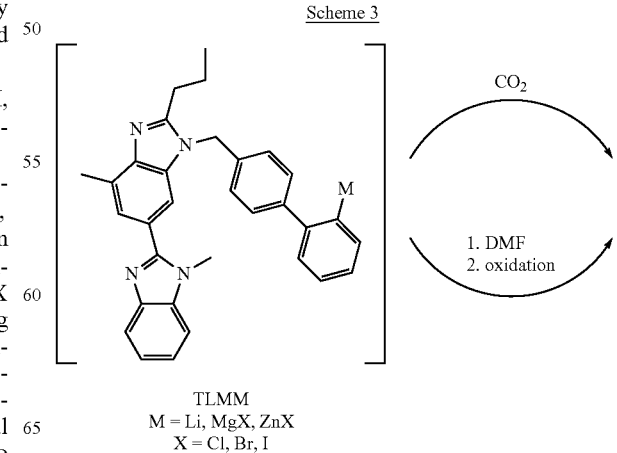

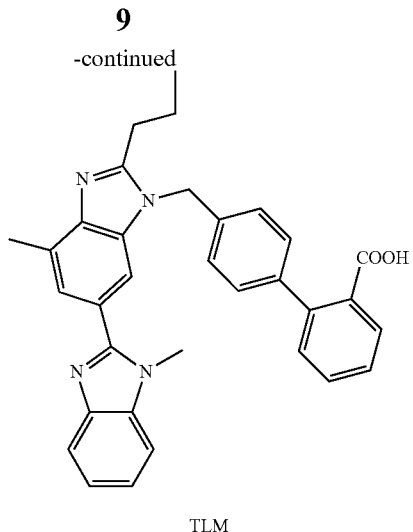

TLM

Organomagnesium compounds are prepared as Grignard reagents of type TLM-MgX (X=Cl, Br, I) by reacting magnesium with the halo compound TLMH, optionally in the presence of a catalyst, preferably iodine or 1,2-dibromoethane. Alternatively Grignard intermediates TLM-MgX are prepared with halogen/metal-exchange reaction with another commercial Grignard reagent.

Organolithium reagent of type TLM-Li is preferably prepared from TLMH by halogen/metal-exchange reaction with elemental lithium or by translithiation with another organolithium compound preferably with carbyllithium, preferably aryllithium or alkyllithium, more preferably phenyllithium or butyllithium, most preferably butyllithium.

Organozinc reagents of type TLM-ZnX (X is selected from iodo, bromo or chloro) can be prepared from TLMH and zinc or its derivative but are preferably prepared from organometal intermediates of type TLM-MgX or TLM-Li and anhydrous zinc halogenide selected from chloride, bromide or iodide.

Organometallic compound is preferably prepared in situ in anhydrous solvents preferably selected from ethers and is converted to telmisartan by bubbling of carbon dioxide or stirred with a solid carbon dioxide (dry ice) at temperature from −50° C. to boiling point, preferably at room temperature for 5 min to 10 h preferably 2 to 4 hours.

In a special but not limited example a solution of TLMH in an above mentioned ether solvent is treated with alkyl lithium preferably butyl lithium at the temperature bellow 0° C., preferably below −40° C. to provide halogen lithium exchange. Following that the prepared solution is bubbled with carbon dioxide gas ($CO_2$) or stirred with a solid carbon dioxide (dry ice) for 5 to 300 minutes. The diluted HCl or $NH_4Cl$ is added and telmisartan is precipitated and filtered off. The cake is washed with water and telmisartan isolated.

In the alternative reaction the above described organometallic intermediates are treated by formic acid derivatives such as esters and amides, preferably N,N-dimethylformamide to give telmisartan aldehyde precursor which can be further oxidized to telmisartan.

In a special but not limited example the above described organolithium solution is quenched with N,N-dimethylformamide at the temperature bellow 0° C., preferably slowly rising temperature from below −40° C. to room temperature to obtain 3'-(2'-formyl-biphenyl-4-ylmethyl)-1,7'-dimethyl-2'-propyl-1H,3'H-[2,5']bibenzoimidazolyl which is converted to telmisartan by oxidation with manganese like manganese (IV) oxide and potassium permanganate, chromium (VI) oxidants like sodium chromate or chromium (VI) oxide adducts, peroxides like hydrogene peroxide in water, low alkanoic acids or alcohols or organic peroxides like alkyl peroxides or carboxylic peroxoacids or higher oxidation state chlorine compounds like metal or organic hypochlorites or sodium chlorate (III) or bromo compounds like bromine, N-bromosuccinimide, inorganic peroxo salts like potassium peroxodisulfate, potassium peroxomonosulfate known under tradename OXONE® or sodium perborate or silver oxyde or oxygene or the like. Preferably sodium chlorate (III) with hydrogene peroxide is used.

In another embodiment the invention also provides for simple preparation of other angiotensin II antagonists like losartan, irbesartan, candesartan, olmesartan and valsartan, which have a residue such as heterocycle or amino acid derivative via methylene linked to a biphenyl and which include a tetrazole substituent on biphenyl in-lieu of carboxylic acid. For those 4'-halomethyl-2-halo-biphenyl is coupled with appropriate residue, which could be prepared or obtained as defined by general knowledge and well-known to the person versed in the art, and biphenylic halo substituent converted into tetrazole as shown in Scheme 4.

Base can be selected from inorganic base such as, sodium hydroxide, potassium hydroxide and the like. $R_3$ in the Scheme 4 represents alkyl.

Scheme 4

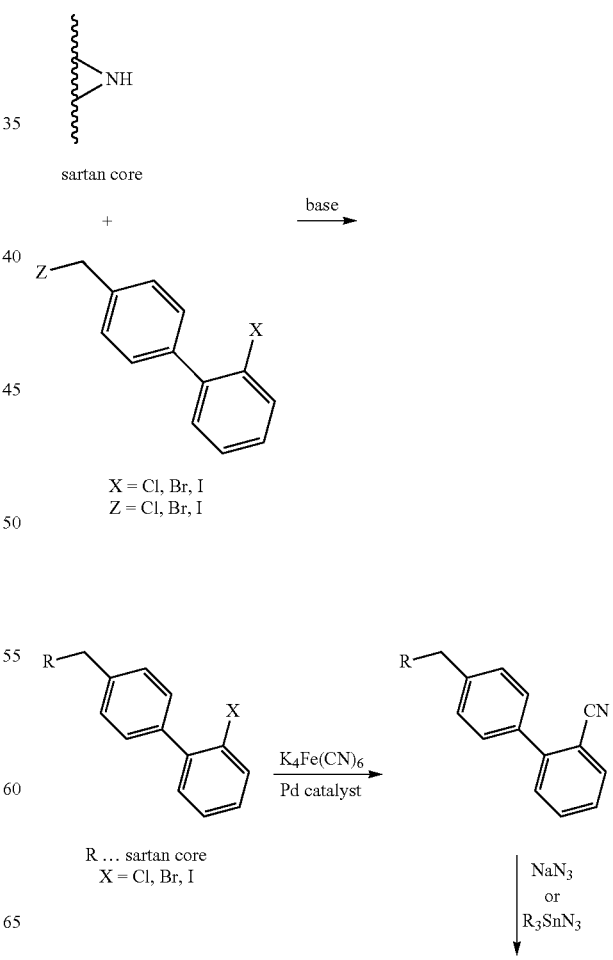

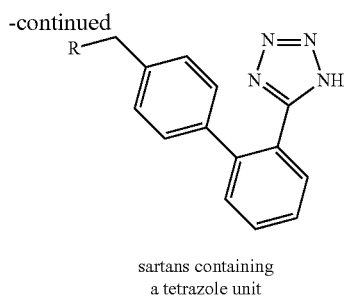

sartans containing
a tetrazole unit

The overall processes of present invention utilize series of Grignard reactions which allows unification of solvents and solvent conditions, furthermore the concentration of components in the reaction mixture is in an aspect of the invention advantageously monitored by the use of in line Fourier transform infrared spectroscopy (FTIR) analytic, thus allowing the adjustment of reaction times and temperatures in real-time or very near real-time. By using a FTIR spectrophotometer it is possible to explore the kinetics of the organic chemical reactions that are not photoinitiated and do not have convenient ultraviolet-visible spectral features. FTIR analytic allows to measure rates, reaction process, end points and mechanisms of the reactions in a solution. FTIR analytics can be employed by using fiber-optic probe attached to a spectrometer, installed to the reaction mixture container, wherein the probe or a spectrometer can be controlled by a desktop computer running supporting software. FTIR is especially suitable In line analytic (ATR FTIR probe) is used to monitor the reactions and single components (reactants, intermediates, product and impurities) and/or to adjust reaction time or reaction temperatures. The background of air is used. The following peaks (heights calculated to single baseline) are monitored: 3242 $cm^{-1}$, 2339 $cm^{-1}$, 1509 $cm^{-1}$, 1486 $cm^{-1}$, 1405 $cm^{-1}$, 1393 $cm^{-1}$, 1227 $cm^{-1}$, 1039 $cm^{-1}$, 1034 $cm^{-1}$, 883 $cm^{-1}$, 880 $cm^{-1}$, 826 $cm^{-1}$, 802 $cm^{-1}$, 783 $cm^{-1}$, 752 $cm^{-1}$, 764 $cm^{-1}$, 721 $cm^{-1}$, 694 $cm^{-1}$. The $1^{st}$ and $2^{nd}$ derivative tools a subtraction tools are used to isolate the component peaks from the IR spectrum of the reaction mixture.

The peaks at 783 $cm^{-1}$ and 1227 $cm^{-1}$ represent the p-toluyl magnesium halide, the peaks at 1035 $cm^{-1}$ and 880 $cm^{-1}$ represent the ether complex of a Grignard and the peak at 695 $cm^{-1}$ is intermediate (1-halophenyl-2-magnesium halide). The reaction is finished when the peak at 695 $cm^{-1}$ disappears.

Thus, another embodiment of the present invention is the process for sartan compounds or 2'-halo-4-methylbiphenyls comprising organometal intermediates, wherein the reaction or single component is monitored with in line FTIR analytics. 2'-halo-4-methylbiphenyls can be prepared according to process comprising reacting 4-halotoluene with a 1,2-dihalobenzene in the presence of metal such as magnesium, lithium or zinc, which already suffices for introduction of in line FTIR analytics. Especially when arisen organometal intermediate is quenched by elemental halogen, providing additional signal to be monitored during the reaction. The inline FTIR analytics can be efficiently utilized also in the processes for obtaining sartans such as telmisartan, losartan, irbesartan, valsartan, olmesartan, candesartan, where the use of organometal intermediates in obtaining 2'-halo-4-methylbiphenyls precedes or is subsequently followed by reaction steps that afford sartan. For example telmisartan or salt thereof can be prepared by a process comprising converting 3'-(2'-halo-biphenyl-4-ylmethyl)-1,7'-dimethyl-2'-propyl-1H,3'H-[2,5']bibenzoimidazolyl to organometallic compound and further reacting said organometallic compound with formic acid derivative or carbon dioxide. As an example N,N-dimethylformamide, alkylformiate can be used as a formic derivative. Specifically, 3'-(2'-halo-biphenyl-4-ylmethyl)-1,7'-dimethyl-2'-propyl-1H,3'H-[2,5']bibenzoimidazolyl can be converted with magnesium to Grignard reagent, or with Grignard reagent by halogen/metal-exchange reaction to another Grignard reagent, or with lithium to organolithium reagent, or with organolithium reagent by halogen/metal-exchange reaction to another organolithium or with zinc to organozinc reagent. The utilization of in line FTIR analytics in the process for preparing sartans in combination with said organometallic compound has an advantageous effect, as it enables to accurately lead the synthesis process in the controllable and efficient manner. Further embodiment of the invention is a container comprising reaction mixture in combination with a FTIR probe, wherein the reaction mixture comprises organometal intermediate or metal reagent and the desired end product of the reaction is selected from the group consisting of telmisartan, losartan, irbesartan, candesartan, olmesartan, valsartan and tasosartan, or intermediate, salt, ester or amide thereof. Organometal intermediate or metal reagent can be Grignard reagent, lithium, organolithium reagent, zinc, organozinc reagent, or the like.

Additionally or alternatively the redox electrode is used to trace the concentration of iodine, bromine or chlorine.

Additional embodiment of the invention is a process for obtaining a pharmaceutical composition and/or dosage form comprising obtaining 2'-halo-4-methylbiphenyls, wherein 4-halotoluene is reacted with a 1,2-dihalobenzene in the presence of magnesium, lithium, zinc, cobalt or copper, and optionally a catalyst, wherein less than 1 molar excess of 4-halotoluene in regard to 1,2-dihalobenzene is used, and converting it to telmisartan; or preparing telmisartan or salt thereof comprising converting 3'-(2'-halo-biphenyl-4-ylmethyl)-1,7'-dimethyl-2'-propyl-1H,3'H-[2,5']bibenzoimidazolyl to organometallic compound and further reacting said organometallic compound with formic acid ester and amide and further oxidation of aldehyde, or with carbon dioxide; and mixing it, optionally in combination with another active pharmaceutical ingredient, with pharmaceutical excipient. The processes of preparing telmisartan, wherein organometal intermediate or metal reagent is applied, can comprise subsequent steps of mixing said telmisartan, optionally together with another active pharmaceutical ingredient, with pharmaceutical excipient. Organometal intermediate can be for example Grignard reagent, organolithium reagent or organozinc reagent. Metal reagent can be for example lithium or zinc. Suitable pharmaceutical excipients are for example binders (e.g. polyvinylpyrrolidon), disintegrators (e.g. starch, cellulose derivatives), surfactants (e.g. sodium laurylsulphate), pH balancing agents (e.g. citric acid, sodium hydroxide, meglumine), fillers (e.g. mannitol, cellulose derivatives), vehicles (e.g. water, glycerol, alcohol), flavors, colorants (e.g. titanium dioxide). The reason for introducing additional active pharmaceutical ingredient into pharmaceutical composition and/or dosage form together with telmisartan is to achieve synergistic effect of both active pharmaceutical ingredients, or having a goal of addressing two indications simultaneously, or to reduce side effects of the first active pharmaceutical ingredient with the simultaneous or consecutive application of the second active pharmaceutical ingredient, or the like. For example, another active pharmaceutical ingredient can be hydrochlorothiazide, amlodipine or ramipril. The technology used for preparing pharmaceutical formulations and/or dosage forms can be any one known to the person skilled in the pharmaceutical technology. Telmisartan, excipients and optionally another active pharmaceutical ingredient can be simply mixed as powders or dissolved in a suitable solvent. Granulation techniques can be applied to improve the handling properties of said formulation. Dry granulation with compacting or briquetting can be undertaken to prime the granulation mass for tabletting. Similarly, wet granulation with adding or spraying granulation liquid onto particles, powders or already dry granules of compounds can be used to aid formulation of the compounds in the dosage form. Granulation techniques can be used to improve flowability, compressibility, especially when the mass is intended to be used for tabletting. Granulation can also reduce dusting and can determine the dissolution properties. Such properties are desired not only with tablets but also in capsules. It is known, that dosage forms can be in a form of tablets, capsules, pellets, granules, powders, solutions, or the like, wherein solid dosage forms can further be coated or layered. Apparatus such as mixer, tabletting machine, extrudor, granulator can be used in preparing the pharmaceutical composition and/or dosage form. Any process according to the present invention, compound of formula 4, any of the aforementioned 4'-halomethyl-2-halo-biphenyl, or preparing the pharmaceutical composition and/or dosage form can be used for preparing a medicament, meaning that said process of preparing pharmaceutical composition and/or dosage form is expanded to embrace necessary steps for preparing a medicament. Said steps can include determination of the right amount of active pharmaceutical ingredient in the pharmaceutical composition and/or dosage form, packaging, or combining the pharmaceutical composition and/or dosage form with a product leaflet.

The following examples illustrate the present invention and are not intended to limit the scope of the invention.

EXAMPLE 1

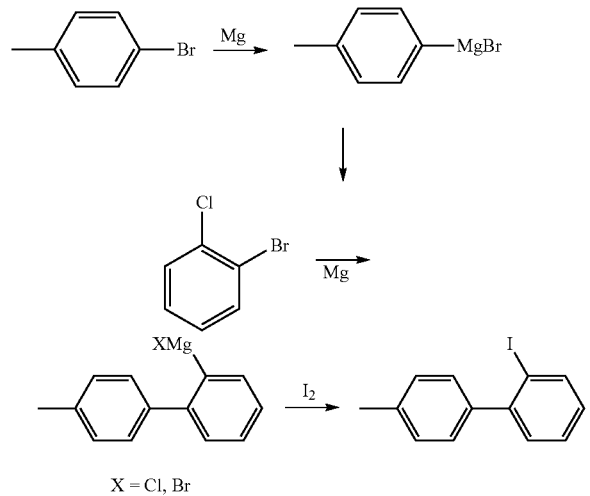

X = Cl, Br

Formation of Grignard Reagent 60 mL of tetrahydrofuran is charged to the flask. 9 g (52.6 mmol) of p-bromotoluene is added and the solution is maintained at 20° C. 3.0 g (125 mmol) of Mg is added and stirred for minimal 30 minutes.

Coupling 9.3 g (48.7 mmol) of 1-bromo-2-chlorobenzene in 5 mL of THF is added into the prepared reaction mixture of p-toluyl magnesium bromide and remaining magnesium at 55° C. in 2 hours and stirred at 55° C. for 2 hours.

Quenching

The prepared solution of 2-magnesium bromide-4'-methyl-biphenyl is cooled to room temperature, and 20 mL of tetrahydrofuran with further 12.3 g (48.7 mmol) of iodine ($I_2$) are added. The mixture is agitated for minimum 5 minutes. The remaining iodine in neutralised with aqueous solution of $NaHSO_3$. 70 mL of demineralised water and 50 mL of n-hexane are added. The phases are separated and the upper (n-hexane) phase is evaporated. The 15.6 g of yellowish liquid is obtained.

The product is purified with LPLC chromatography. Mobile phase is n-hexane, stationary phase is silicagel 60. The fractions are collected. The main fractions are evaporated. 8.6 g (60%) of 2-iodo-4'methyl-biphenyl (colourless liquid) is obtained.

$^1$H NMR (300 MHz, $CDCl_3$) δ: 2.56 (s, 3H), 7.13 (dt, J=7.5 Hz, J=2.0 Hz, 1H), 7.39 (s, 4H), 7.44 (dd, J=7.6 Hz, J=1.9 Hz, 1H), 7.47-7.52 (m, 1H), 8.09 (dd, J=7.9 Hz, J=1.0 Hz, 1H). $^{13}$C NMR (75 MHz, $CDCl_3$) δ: 146.4, 141.2, 139.3, 137.1, 130.0, 129.0, 128.5, 128.5, 128.0, 98.8, 21.2.

EXAMPLE 2

Bromination of 2-iodo-4'-methyl-biphenyl

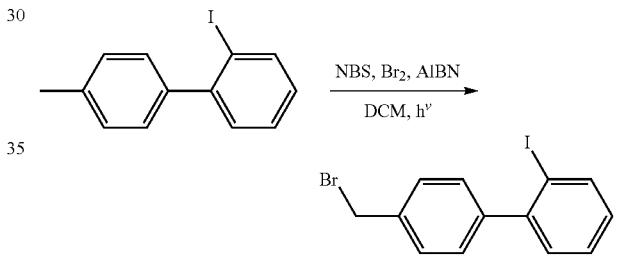

20 mL of dichloromethane (DCM) is charged to the flask. 0.73 g of N-bromosuccinimide (NBS), 0.08 g of 2,2'-azoisobutyronitrile (AIBN), 18 µL of $Br_2$ and 0.9 g of 2-iodo-4'-methyl-biphenyl are added. The reaction is carried out under reflux temperature for minimum 2 hours and the flask is lighted all the time. The reaction is quenched with aqueous solution of $Na_2S_2O_3$. The phases are separated and the lower DCM phase is washed with demineralised water one more time. The DCM phase is evaporated and 4 mL of n-hexane is charged and stirred at room temperature for 30 minutes. The suspension is then cooled to 0° C. and filtered. The cake is washed with 2 mL of solvent. 0.6 g of white crystals of 4'-bromomethyl-2-iodo-biphenyl is obtained.

$^1$H NMR (300 MHz, $CDCl_3$) δ: 4.58 (s, 2H), 7.06 (dt, J=7.6 Hz, J=1.8 Hz, 1H), 7.31 (dd, J=7.7 Hz, J=1.8 Hz, 1H), 7.35 (d, J=8.2 Hz, 2H), 7.40 (dt, J=7.4 Hz, J=1.2 Hz, 1H), 7.48 (d, J=8.2 Hz, 2H), 7.98 (dd, J=7.9 Hz, J=1.1 Hz, 1H). $^{13}$C NMR (75 MHz, $CDCl_3$) δ: 145.8, 144.1, 139.5, 137.0, 130.0, 129.6, 128.9, 128.6, 128.1, 98.3, 33.2.

EXAMPLE 3

Bromination of 2-iodo-4'-methyl-biphenyl 15.9 g of 2-iodo-4'-methyl-biphenyl is dissolved in 140 mL of dichloromethane (DCM) than 0.7 g of 2,2'-azoisobutyronitrile (AIBN), and slowly first 1.83 mL and after 1 h additional 1.14 ml of Br$_2$ are added. The reaction is carried out under reflux temperature for 5 hours and the flask is lighted all the time. The reaction is quenched with aqueous solution of Na$_2$S$_2$O$_3$. The phases are separated and the lower DCM phase is washed with demineralised water one more time. The DCM phase is evaporated and 40 mL of n-hexane is charged and stirred at 40° C. for 30 minutes. The suspension is then cooled to 0° C. and filtered. The cake is washed with 15 mL of hexane and 11.0 g of white crystals of 4'-bromomethyl-2-iodo-biphenyl is obtained.

$^1$H NMR (300 MHz, CDCl$_3$) δ: 4.58 (s, 2H), 7.06 (dt, J=7.6 Hz, J=1.8 Hz, 1H), 7.31 (dd, J=7.7 Hz, J=1.8 Hz, 1H), 7.35 (d, J=8.2 Hz, 2H), 7.40 (dt, J=7.4 Hz, J=1.2 Hz, 1H), 7.48 (d, J=8.2 Hz, 2H), 7.98 (dd, J=7.9 Hz, J=1.1 Hz, 1H). $^{13}$C NMR (75 MHz, CDCl$_3$) δ: 145.8, 144.1, 139.5, 137.0, 130.0, 129.6, 128.9, 128.6, 128.1, 98.3, 33.2.

EXAMPLE 4

Alkylation of (2-(1-propyl)-4-methyl-6-(1'-methyl-benzimidazole-2-il)benzimidazole)

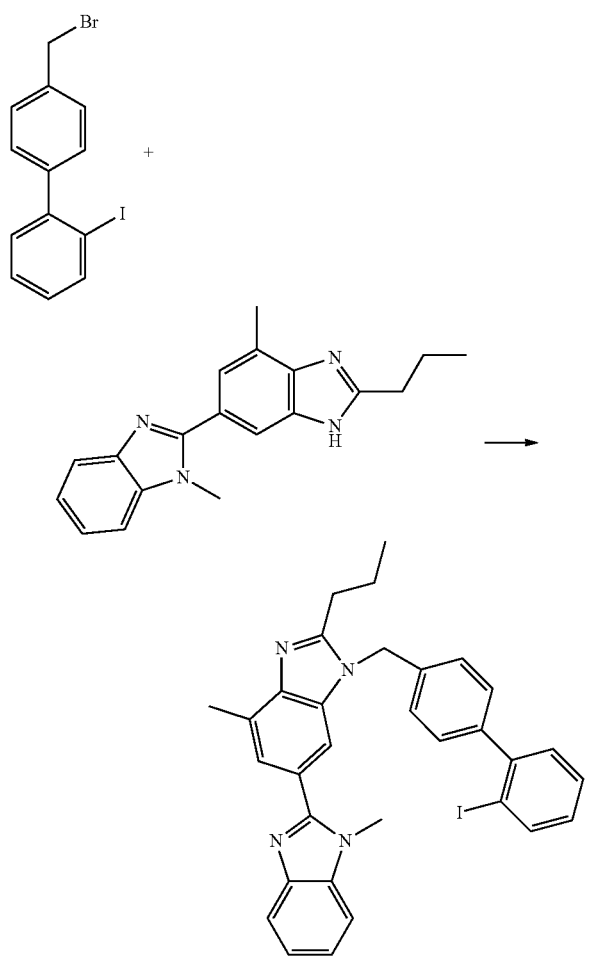

15 mL of sulfolane (tetramethylene sulfone) is charged to the flask. 0.85 g of PMB (2-(1-propyl)-4-methyl-6-(1'-methylbenzimidazole-2-il)benzimidazole) and 0.38 g of potassium tert-butoxide are added. The mixture is heated above 30° C. to dissolve all the components. The solution is than cooled down to 15° C. and 1.07 g of 4'-bromomethyl-2-iodo-biphenyl in 5 mL of solvent is added slowly during 45 minutes. The reaction mixture is stirred at the same temperature for additional 2 hours. 40 mL of demineralised water and 35 mL of EtOAc (ethyl acetate) are added. The phases are separated. The upper EtOAc phase is washed several times with saturated water solution of NaCl. The solvent is evaporated and 4 mL mixture of EtOAc and acetone is added. The suspension is stirred for 30 minutes at room temperature. The suspension is filtered and 0.94 g of white crystals of 3'-(2'-iodo-biphenyl-4-ylmethyl)-1,7'-dimethyl-2'-propyl-1H,3'H-[2,5']bibenzimidazolyl are obtained.

$^1$H NMR (300 MHz, CDCl$_3$) δ: 1.06 (t, J=7.4 Hz, 3H), 1.84-1.92 (m, 2H), 2.95 (t, J=7.8 Hz, 2H), 3.81 (s, 3H), 5.46 (s, 2H), 7.03 (ddd, J=7.9 Hz, J=7.4 Hz, J=1.8 Hz, 1H), 7.13 (d, J=8.0 Hz, 2H), 7.23-7.54 (m, 9H), 7.77-7.83 (m, 1H), 7.94 (dd, J=7.9 Hz, J=1.1 Hz, 1H).

EXAMPLE 5

Synthesis of Telmisartan

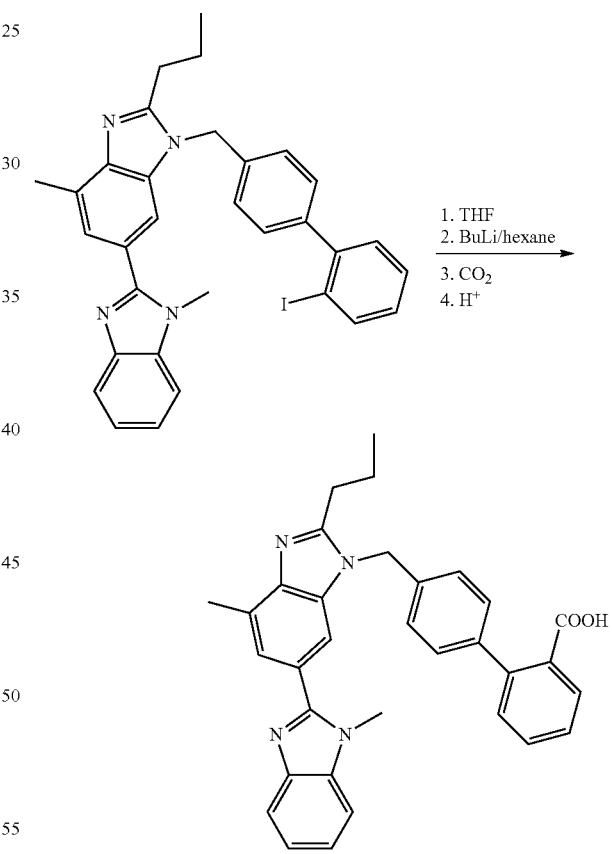

0.5 g of 3'-(2'-iodo-biphenyl-4-ylmethyl)-1,7'-dimethyl-2'-propyl-1H,3'H-[2,5']bibenzoimidazolyl is dissolved in 10 mL of THF and the solution is cooled to temperature of −60° C. to −70° C. 0.58 mL of 1.6 M solution of butyl lithium in hexane is slowly added to the solution and the reaction mixture is stirred for 15 min at the same temperature.

Separately dried powdered CO$_2$ was suspended in approximately 20 ml of THF and the prepared solution of (4'-((1,7'-dimethyl-2'-propyl-1H,3'H-2,5'-benzo[d]imidazol-3'-yl)methyl)biphenyl-2-yl)lithium is slowly added not extending the temperature above −40° C. After finishing the addition the mixture is allowed to be warmed to −10° C. and stirred for 1 h. The diluted HCl is then added and precipitated telmisartan is filtered of. The cake is washed with water. 0.4 g of crude telmisartan (2-[4-[[4-methyl-6-(1-methylbenzoimidazol-2-yl)-2-propyl-benzoimidazol-1-yl]methyl]phenyl]benzoic acid) is obtained.

EXAMPLE 6

Formation of 3'-(2'-formyl-biphenyl-4-ylmethyl)-1,7'-dimethyl-2'-propyl-1H,3'H-[2,5']bibenzoimidazolyl and synthesis of telmirtan

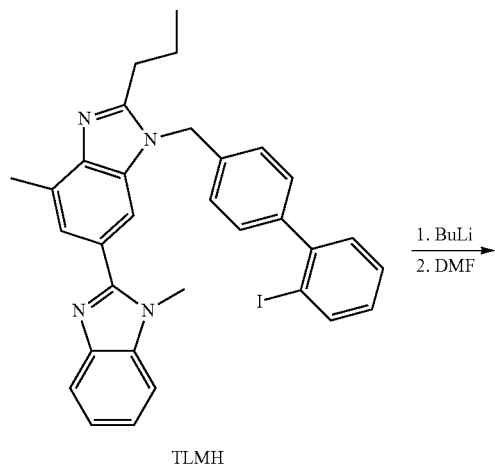

TLMH

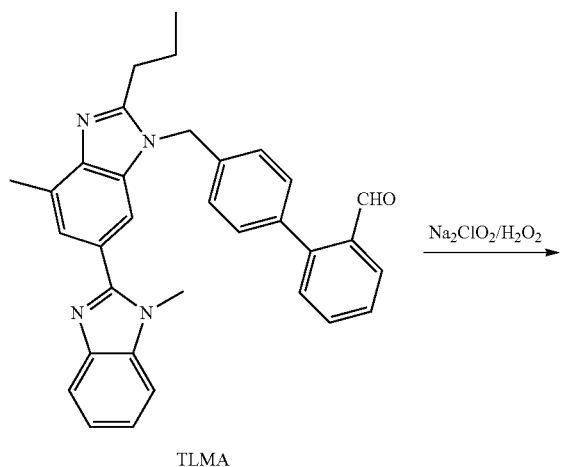

TLMA

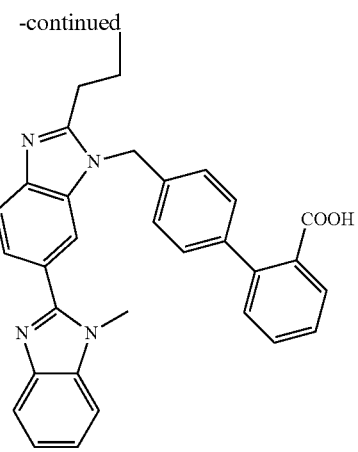

TLM

To a suspension of 3'-(2'-iodo-biphenyl-4-ylmethyl)-1,7'-dimethyl-2'-propyl-1H,3'H-[2,5']bibenzoimidazolyl (460 mg) in toluene (13 mL) is added 1.6 M BuLi in hexane (0.56 mL) within 60 min at room temperature. After 60 h, dimethylformamide (DMF; 0.2 mL) is added all at once and the mixture is stirred for an additional 24 h. Water (4 mL) is added, the phases are separated and extracted 4 times with 9 mL of ethyl acetate. Combined organic extracts are dried over MgSO$_4$ and evaporated under reduced pressure to obtain 230 mg of TLMA as crude amorphous product.

A solution of 156 mg of NaClO$_2$.4H$_2$O in 1 mL of water was added dropwise by canilla to a stirred mixture of 4'-[(2-n-propyl-4-methyl-6-(1-methyl-imidazol-4-yl)-benzimidazol-1-yl)methyl]-biphenyl-2-carboxaldehyde (230 mg) in 1 mL of acetonitrile, 0.16 ml of 10 solution of NaH$_2$PO$_4$ in water and 0.23 mL of 30% H$_2$O$_2$ at the temperature 10° C. pH of the mixture was adjusted to 2 with concentrated hydrochloric acid. Stirring was continued for 1.5 h at room temperature. Reaction mixture was poured in 1.2 mL of water, stirred for 15 minutes, product filtered, washed with water and dried in vacuo to yield 210 mg of telmisartan.

The invention claimed is:

1. A process for obtaining telmisartan or salt thereof, comprising converting 3'-(2'-halo-biphenyl-4-ylmethyl)-1,7'-dimethyl-2'-propyl-1H,3'H-[2,5']bibenzoimidazolyl to an organometallic compound, reacting said organometallic compound with carbon dioxide to form telmisartan, or reacting said organometallic compound with formic acid ester or amide forming a telmisartan aldehyde precursor, and oxidizing said telmisartan aldehyde precursor to form telmisartan.

2. The process according to claim 1, wherein formic acid ester or amide is N,N-alkylformiate or dimethylformamide.

3. The process according to claim 1, wherein 3'-(2'-halo-biphenyl-4-ylmethyl)-1,7'-dimethyl-2'-propyl-1H,3'H-[2,5'] bibenzoimidazolyl is converted with magnesium to Grignard reagent, or with Grignard reagent by halogen/metal-exchange reaction to another Grignard reagent, or with zinc to organozinc reagent; or is converted with lithium to organolithium reagent, or is converted with organolithium reagent by halogen/metal-exchange reaction to another organolithium reagent.

4. A process for obtaining a pharmaceutical composition and/or dosage form comprising preparing telmisartan or salt thereof according to claim 1; and mixing it, optionally in combination with another active pharmaceutical ingredient, with pharmaceutical excipient.

* * * * *